(12) United States Patent
Nishi (10) Patent No.: US 10,722,203 B2
(45) Date of Patent: Jul. 28, 2020

(54) MAMMOGRAPHY APPARATUS

(71) Applicant: FUJIFILM CORPORATION, Minato-ku, Tokyo (JP)

(72) Inventor: Yoshihiro Nishi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 217 days.

(21) Appl. No.: 15/922,946

(22) Filed: Mar. 16, 2018

(65) Prior Publication Data

US 2018/0271467 A1 Sep. 27, 2018

(30) Foreign Application Priority Data

Mar. 22, 2017 (JP) ................................. 2017-056554

(51) Int. Cl.
*A61B 6/00* (2006.01)
*A61B 6/02* (2006.01)
*H05G 1/00* (2006.01)

(52) U.S. Cl.
CPC .............. *A61B 6/502* (2013.01); *A61B 6/025* (2013.01); *A61B 6/405* (2013.01); *A61B 6/4035* (2013.01);
(Continued)

(58) Field of Classification Search
CPC ......... A61B 6/025; A61B 6/08; A61B 6/4007; A61B 6/4035; A61B 6/4042; A61B 6/405;
(Continued)

(56) References Cited

U.S. PATENT DOCUMENTS 4,763,343 A * 8/1988 Yanaki .................. A61B 6/502
378/110
5,812,629 A * 9/1998 Clauser .................. A61B 6/032
378/37
(Continued)

FOREIGN PATENT DOCUMENTS

JP S60-92507 U 6/1985
JP H03-19843 Y2 4/1991
(Continued)

OTHER PUBLICATIONS

Extended European Search Report dated Jul. 13, 2018, issued in corresponding EP Patent Application No. 18160634.4.
(Continued)

*Primary Examiner* — Blake C Riddick
(74) *Attorney, Agent, or Firm* — SOLARIS Intellectual Property Group, PLLC (57) ABSTRACT

Provided is a mammography apparatus capable of reducing an increase in the size of an entire apparatus in a case where a plurality of filters and a mirror are provided. A mammography apparatus includes a radiation source that emits radiation toward an imaging stand, a visible light source that is provided outside an irradiation field of the radiation emitted from the radiation source and emits visible light, a first filter that includes an Rh filter and an Al filter as a plurality of filters that is selectively used according to the kind of imaging, and a mirror part that is provided between the radiation source and the imaging stand, includes a Cu filter used in a case where contrast imaging is performed, reflects the visible light toward imaging stand, and is movable between a position inside the irradiation field and a position outside the irradiation field.

14 Claims, 9 Drawing Sheets

(52) U.S. Cl.
CPC ............ *A61B 6/4042* (2013.01); *A61B 6/481* (2013.01); *A61B 6/482* (2013.01); *H05G 1/00* (2013.01)

(58) Field of Classification Search
CPC ......... A61B 6/481; A61B 6/482; A61B 6/502; A61B 6/542; H05G 1/00
See application file for complete search history.

(56) References Cited

U.S. PATENT DOCUMENTS

| | | | | |
|---|---|---|---|---|
| 5,938,613 | A * | 8/1999 | Shmulewitz | A61B 6/502 128/915 |
| 6,435,717 | B1 * | 8/2002 | Kohler | A61B 6/107 378/205 |
| 2002/0070365 | A1 * | 6/2002 | Karellas | A61B 6/06 250/581 |
| 2003/0205675 | A1 * | 11/2003 | Nelson | A61B 6/4233 250/370.09 |
| 2004/0131145 | A1 * | 7/2004 | Ohara | A61B 6/0414 378/37 |
| 2004/0161075 | A1 * | 8/2004 | Amitani | A61B 6/0457 378/37 |
| 2007/0183565 | A1 | 8/2007 | Brandstatter et al. | |
| 2008/0101537 | A1 * | 5/2008 | Sendai | A61B 6/025 378/23 |
| 2008/0198968 | A1 * | 8/2008 | Takekoshi | A61B 6/4441 378/62 |
| 2008/0279330 | A1 * | 11/2008 | Ueki | A61B 5/0091 378/63 |
| 2009/0190720 | A1 * | 7/2009 | Windt | A61B 6/4021 378/146 |
| 2009/0190722 | A1 * | 7/2009 | Windt | A61B 6/08 378/206 |
| 2009/0290679 | A1 | 11/2009 | Mikami et al. | |
| 2010/0080436 | A1 * | 4/2010 | Ohara | A61B 6/06 382/132 |
| 2010/0189214 | A1 * | 7/2010 | Shibata | A61B 6/025 378/21 |
| 2012/0020454 | A1 * | 1/2012 | Murakoshi | G21K 1/025 378/36 |
| 2012/0069957 | A1 * | 3/2012 | Nakayama | A61B 6/022 378/21 |
| 2012/0099705 | A1 * | 4/2012 | Murakoshi | A61B 6/4291 378/85 |
| 2012/0140883 | A1 * | 6/2012 | Iwakiri | A61B 6/4233 378/62 |
| 2012/0140885 | A1 * | 6/2012 | Iwakiri | A61B 6/06 378/62 |
| 2012/0145912 | A1 * | 6/2012 | Iwakiri | A61B 6/06 250/370.08 |
| 2012/0153177 | A1 * | 6/2012 | Iwakiri | A61B 6/4291 250/370.09 |
| 2012/0163537 | A1 * | 6/2012 | Iwakiri | A61B 6/4283 378/62 |
| 2012/0238870 | A1 | 9/2012 | Smith et al. | |
| 2013/0077744 | A1 * | 3/2013 | Kamiya | A61B 6/5241 378/62 |
| 2013/0121464 | A1 * | 5/2013 | Tajima | A61B 6/542 378/62 |
| 2013/0182823 | A1 * | 7/2013 | Kuwabara | A61B 6/542 378/62 |
| 2013/0299710 | A1 * | 11/2013 | Uchida | G01T 1/202 250/366 |
| 2014/0086382 | A1 * | 3/2014 | Flohr | A61B 6/032 378/5 |
| 2014/0103220 | A1 * | 4/2014 | Ohta | A61B 6/4266 250/366 |
| 2014/0103222 | A1 * | 4/2014 | Ohta | A61B 6/025 250/393 |
| 2014/0126697 | A1 * | 5/2014 | Ohashi | A61B 6/08 378/62 |
| 2014/0205066 | A1 * | 7/2014 | Kitagawa | A61B 6/542 378/62 |
| 2014/0241500 | A1 * | 8/2014 | Yasuda | A61B 6/06 378/62 |
| 2014/0321611 | A1 * | 10/2014 | Cho | A61B 6/405 378/20 |
| 2015/0131776 | A1 * | 5/2015 | Cho | G01N 23/02 378/19 |
| 2015/0269766 | A1 * | 9/2015 | Kobayashi | A61B 6/502 345/419 |

FOREIGN PATENT DOCUMENTS

| | | |
|---|---|---|
| JP | H05-183817 A | 7/1993 |
| JP | 2000-102534 A | 4/2000 |
| JP | 2005-006971 A | 1/2005 |
| JP | 2005-342363 A | 12/2005 |
| JP | 2009-279111 A | 12/2009 |
| JP | 2012-055420 A | 3/2012 |
| JP | 2014-507250 A | 3/2014 |
| JP | 2014-166276 A | 9/2014 |

OTHER PUBLICATIONS

English language translation of the following: Office action dated Jan. 7, 2020 from the JPO in a Japanese patent application No. 2017-056554 corresponding to the instant patent application. This office action translation is submitted now in order to supplement the understanding of the cited references which are being disclosed in the instant Information Disclosure Statement.

* cited by examiner

MAMMOGRAPHY APPARATUS

CROSS-REFERENCE TO RELATED APPLICATION

This application claims priority under 35 USC 119 from Japanese Patent Application No. 2017-056554 filed on Mar. 22, 2017, the disclosure of which is incorporated by reference herein in its entirety.

BACKGROUND OF THE INVENTION

1. Field of the Invention

The present invention relates to a mammography apparatus.

2. Description of the Related Art

A mammography apparatus that emits radiation toward mammae of a test subject from a radiation source and detects the radiation that passes through the mammae using a radiation detector to capture a radiation image is known.

Generally, the radiation emitted from the radiation source of the mammography apparatus is applied to the mammae of the test subject through a filter. Further, generally, in the mammography apparatus, a configuration in which a visible light source that emits visible light in order to show an irradiation range of radiation (irradiation field) using visible light instead of the radiation and a mirror that reflects the visible light emitted from the visible light source toward an imaging stand are provided is also known.

Japanese Examined Utility Model Application Publication No. 3-19843 discloses a mammography apparatus that includes two kinds of filters and a mirror.

SUMMARY OF THE INVENTION

However, in the technique disclosed in JP1991-19843Y (JP-H3-19843Y), in a case where a plurality of filters is further provided, the size of the entire apparatus becomes large.

The invention has been made in consideration of the above-mentioned problem, and an object of the invention is to provide a mammography apparatus capable of reducing an increase in the size of the apparatus in a case where a plurality of filters and a mirror is provided.

According to an aspect of the invention, there is provided a mammography apparatus comprising: a radiation source that emits radiation generated by application of a tube voltage toward an imaging stand; a visible light source that is provided outside an irradiation field of the radiation emitted from the radiation source and emits visible light; a first filter that is provided between the radiation source and the imaging stand and includes a plurality of filters selectively used in a case where a first tube voltage is applied to the radiation source; and a mirror part that is provided between the radiation source and the imaging stand, includes a second filter used in a case where a second tube voltage different from the first tube voltage is applied to the radiation source, reflects the visible light toward the imaging stand, and is movable between a position inside the irradiation field and a position outside the irradiation field.

In the mammography apparatus according to this aspect of the invention, the second tube voltage may be a tube voltage used in contrast imaging.

In the mammography apparatus according to this aspect of the invention, the second tube voltage may be a tube voltage higher than the first tube voltage.

According to another aspect of the invention, there is provided a mammography apparatus comprising: a radiation source that emits radiation toward an imaging stand; a visible light source that is provided outside an irradiation field of the radiation emitted from the radiation source and emits visible light; a first filter that includes a plurality of filters selectively used according to the type of imaging; and a mirror part that is provided between the radiation source and the imaging stand, includes a second filter used in a case where contrast imaging is performed, reflects the visible light toward the imaging stand, and is movable between a position inside the irradiation field and a position outside the irradiation field.

In the mammography apparatus according to these aspects of the invention, the first filter and the second filter may be different from each other in at least one of an absorbance of radiation to be transmitted, an attenuation factor of the radiation, or an energy component of radiation to be absorbed.

In the mammography apparatus according to these aspects of the invention, the mirror part may be configured so that the second filter is disposed on the side of the radiation source and the visible light is emitted toward the imaging stand from the visible light source.

In the mammography apparatus according to these aspects of the invention, the plurality of filters may include a filter used for tomosynthesis imaging.

The mammography apparatus according to these aspects of the invention may further comprise: a first moving part that moves a filter selected from the plurality of filters between a position inside the irradiation field and a position outside the irradiation field.

In the mammography apparatus according to these aspects of the invention, the second filter may be a filter made of copper.

The mammography apparatus according to these aspects of the invention may further comprise: a second moving part that moves the mirror part between a position inside the irradiation field and a position outside the irradiation field.

In the mammography apparatus according to these aspects of the invention, the second moving part may set the position of the mirror part to the position inside the irradiation field in a state where the radiation source does not emit radiation, and may set the position of the mirror part to the position outside the irradiation field in a state where the radiation source emits radiation and the first filter is used.

In the mammography apparatus according to these aspects of the invention, the second moving part may set the position of the mirror part to the position inside the irradiation field in a state where the radiation source does not emit radiation, and may set the position of the mirror part to the position inside the irradiation field in a state where the radiation source emits radiation and the second filter is used.

According to the present disclosure, in a case where a plurality of filters and a mirror are provided, it is possible to reduce an increase in the size of an apparatus.

DESCRIPTION OF THE PREFERRED EMBODIMENTS

Hereinafter, embodiments of the invention will be described in detail with reference to the accompanying drawings. The embodiments do not limit the invention.

First Embodiment

First, an example of an entire configuration of a mammography apparatus according to this embodiment will be described with reference to FIG. 1.

A mammography apparatus 10 according to this embodiment is an apparatus that individually emits radiation (for example, X-rays) to right and left mammae of a test subject to individually capture radiation images of the right and left mammae. The mammography apparatus 10 may be an apparatus that images mammae of a test subject in a state where the test subject is standing (standing position state), or in a state where the test subject sits on a chair (including a wheelchair) (sitting position state). That is, the mammography apparatus 10 may be an apparatus capable of individually imaging at least the right and left mammae of the test subject.

Further, the mammography apparatus 10 according to this embodiment includes three kinds of imaging functions of so-called tomosynthesis imaging (of which details will be described later), so-called contrast imaging performed in a state where a contrast medium is administered to mammae of a test subject, and normal imaging. In this embodiment, the imaging performed in a state where the contrast medium is administered to the mammae of the test subject is referred to as the "contrast imaging", the imaging other than the contrast imaging and the tomosynthesis imaging is referred to as the "normal imaging", and the imaging (tomosynthesis imaging and normal imaging) other than the contrast imaging is collectively referred to as "simple imaging".

In addition, in the following description, it is assumed that a side (breast wall side) close to a test subject in a case where the test subject faces the mammography apparatus 10 in capturing a radiation image is an apparatus front side of the mammography apparatus 10 and a side distant from the test subject in a case where the test subject faces the mammography apparatus 10 is an apparatus rear side of the mammography apparatus 10. Further, in the description, it is assumed that a lateral direction of the test subject in a case where the test subject faces the mammography apparatus 10 is an apparatus lateral direction of the mammography apparatus 10. In addition, in the description, it is assumed that a direction in which the side of the head of the test subject is an upper side and the side of the feet is a lower side in a case where the test subject faces the mammography apparatus 10 is a vertical direction.

Figure 1:
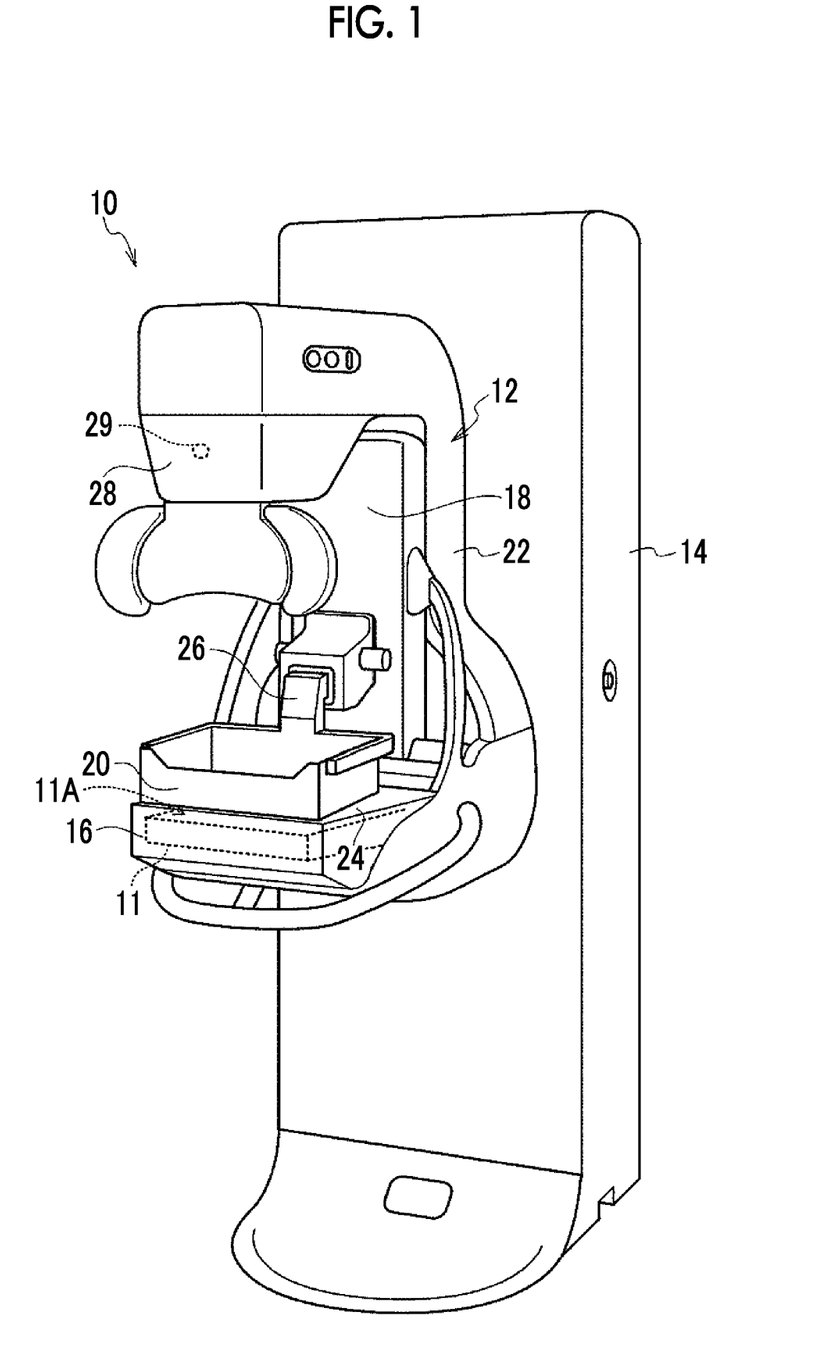
FIG. 1 is a diagram showing an example of an entire configuration of a mammography apparatus according to a first embodiment, which is a perspective view when seen from a breast wall side of a test subject.

As shown in FIG. 1, the mammography apparatus 10 includes an imaging part 12 of an approximately C-shape in a side view, provided in a front part of the apparatus, and a base stand part 14 that supports the imaging part 12 from a rear side of the apparatus.

The imaging part 12 includes an imaging stand 16 having a planar imaging surface 24 that is contiguous to the mammae of the test subject in a standing state, a pressing plate 20 for pressing the mammae in a state where the mammae is interposed between the imaging surface 24 of the imaging stand 16 and the pressing plate 20, and a holding part 18 that supports the imaging stand 16 and the pressing plate 20. A member that transmits radiation is used for the pressing plate 20.

Further, the imaging part 12 includes a radiation irradiation part 28 in which a radiation source 29 including a bulb (in this embodiment, for example, tungsten) that emits radiation to the mammae is provided, and a support part 22 that is spaced from the holding part 18 and supports the radiation source 29.

In addition, a shaft (not shown) is provided in the imaging part 12, so that the imaging part 12 is able to rotate with respect to the base stand part 14. The shaft is fixed with respect to the support part 22, and the shaft and the support part 22 integrally rotate.

Gears are respectively provided in the shaft provided in the imaging part 12 and the holding part 18, and an engagement state and a non-engagement state of the gears are switched, so that a state where the holding part 18 and the shaft are connected to each other to integrally rotate and a state where the shaft is spaced from the holding part 18 to idly rotate can be switched. The switching between transmission of power of the shaft and non-transmission thereof is not limited to the above-mentioned gears, and instead, a variety of machine elements may be used.

The holding part 18 supports the imaging stand 16 and the radiation source 29 while causing the imaging surface 24 and the radiation source 29 to be spaced from each other by a predetermined interval. Further, the holding part 18 also holds the pressing plate 20 through a support arm 26, in which the holding part 18 slides the support arm 26, so that the pressing plate 20 moves, and thus, an interval between the pressing plate 20 and the imaging surface 24 is changed.

The imaging surface 24 onto which the mammae of the test subject are contiguous is formed of carbon, from a viewpoint of radiability or strength, for example. Inside the imaging stand 16, a radiation detector 11 that detects radiation that passes through the mammae and the imaging surface 24 is disposed. A radiation image is generated on the basis of the radiation detected by the radiation detector 11. The type of the radiation detector 11 according to this embodiment is not particularly limited, and for example, may be a radiation detector of an indirect conversion type that converts radiation into light and converts the converted light into electric charges, or may be a radiation detector of a direct conversion type that directly converts radiation into electric charges. In this embodiment, image data indicating a radiation image output from the radiation detector 11 of the mammography apparatus 10 is transmitted to a console 6 (see FIG. 6).

Figure 2:
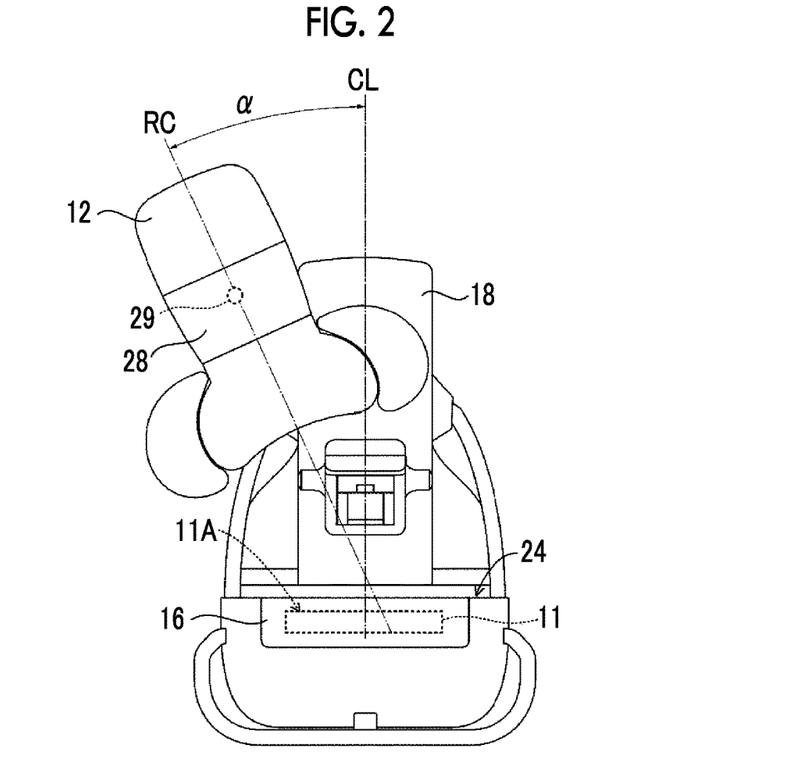
FIG. 2 is a diagram for illustrating tomosynthesis imaging in the mammography apparatus according to the first embodiment.

The mammography apparatus 10 of this embodiment may emit radiation while varying an incidence angle of the radiation in a predetermined range from the radiation source 29, as shown in FIG. 2, and may perform imaging (so-called tomosynthesis imaging) at each of the different incidence angles. Here, the "incidence angle" refers to an angle formed by a normal line CL of a detection surface 11A of the radiation detector 11 and a radiation axis RC. Accordingly, in a case where the normal line CL and the radiation axis RC are the same, the incidence angle becomes 0. Further, here, it is assumed that the detection surface 11A of the radiation detector 11 is a surface that is approximately parallel to the imaging surface 24.

In this embodiment, as shown in FIG. 2, imaging is performed whenever the radiation source 29 is positioned at each of imaging positions of a plurality of places while the position of the radiation source 29 is moving to change the incidence angle of the radiation from an angle α at an interval of a predetermined angle θ.

In the mammography apparatus 10 of this embodiment, in cases other than a case where the incidence angle of radiation is 0, imaging is performed at each imaging position while continuously moving the radiation source 29. As an imaging method in a case where the radiation source 29 is continuously moved, for example, a method for continuously moving the radiation source 29 without stopping, emitting radiation to mammae from the radiation source 29 in a case where the radiation source 29 reaches each imaging position, and performing imaging using the radiation detector 11 in synchronization with a timing of the emission may be used.

Figure 3:
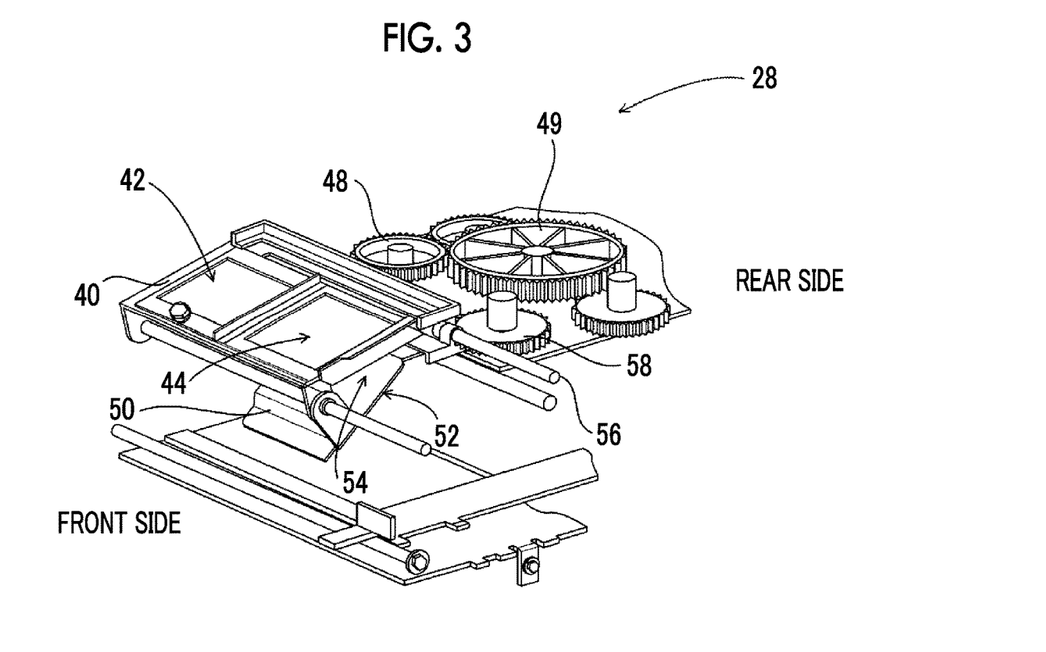
FIG. 3 is a perspective view showing an example of an internal configuration of a radiation irradiation part in the mammography apparatus according to the first embodiment.
Figure 4:
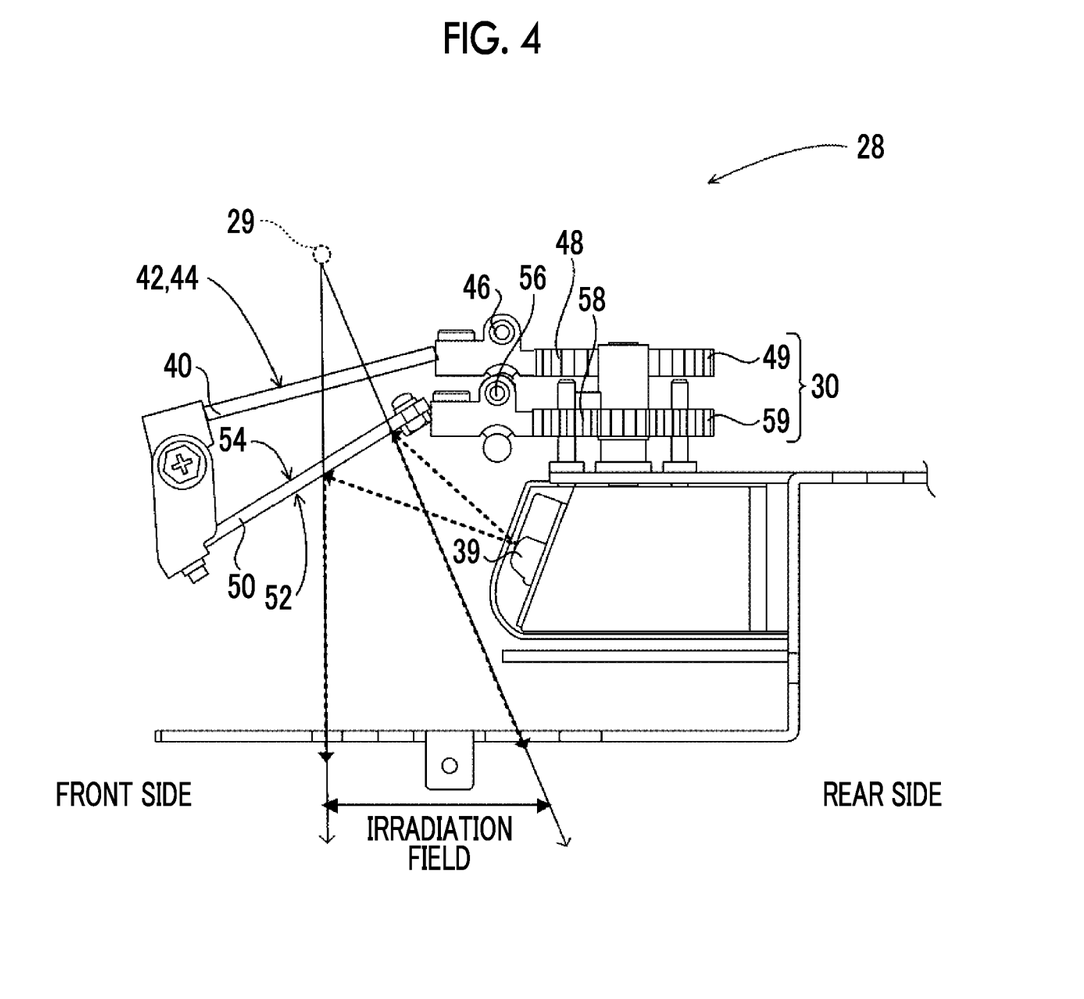
FIG. 4 is a cross-sectional view showing the example of the internal configuration of the radiation irradiation part in the mammography apparatus according to the first embodiment, when seen from a right side of the apparatus.
Figure 5:
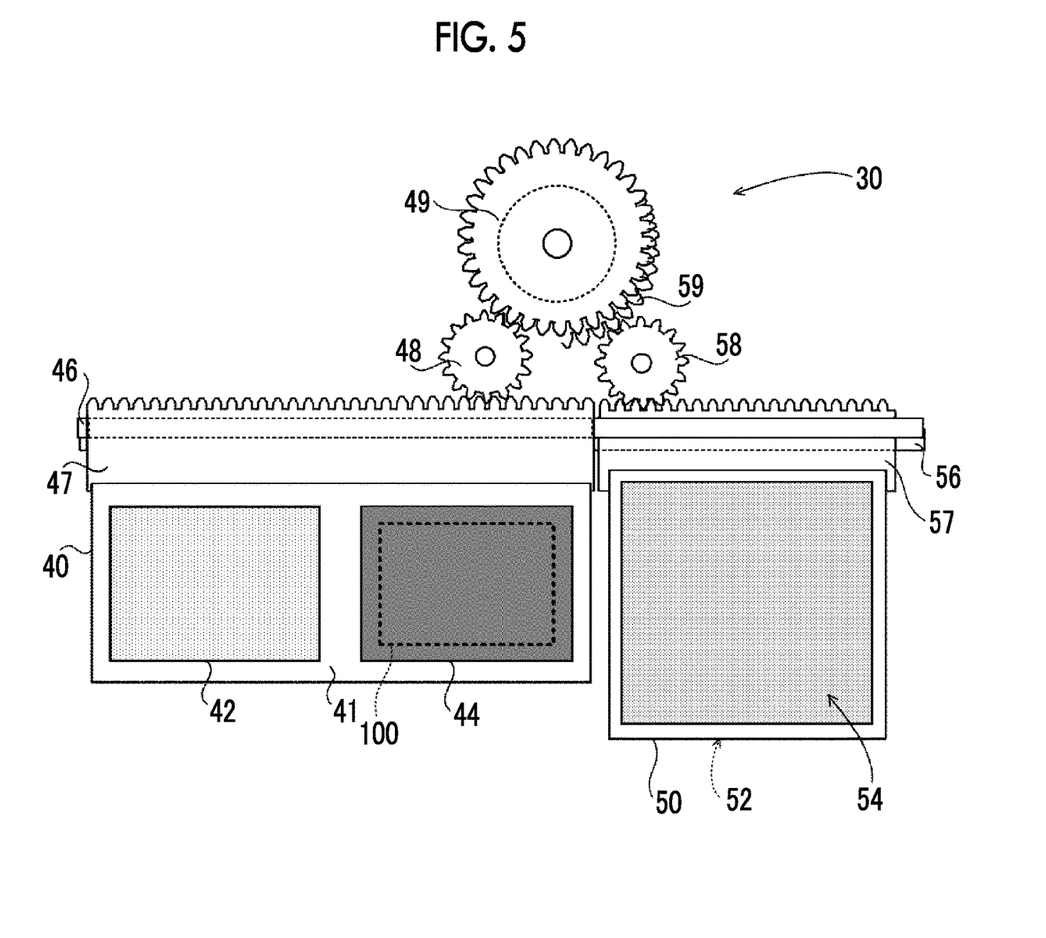
FIG. 5 is a schematic diagram schematically showing a moving part, a first filter, and a mirror part shown in FIGS. 3 and 4, when seen from a radiation source side (upper side) in a planar view.

Next, the radiation irradiation part 28 in the mammography apparatus 10 of this embodiment will be described. Inside the radiation irradiation part 28 of the mammography apparatus 10 of this embodiment, as shown in FIGS. 3 and 4, the radiation source 29, a visible light source 39, a first filter 40, a mirror part 50, and a moving part 30 that moves the first filter 40 and the mirror part 50 are provided. FIG. 5 is a schematic diagram of the moving part 30, the first filter 40, and the mirror part 50 shown in FIGS. 3 and 4, when seen from the side of the radiation source 29 (upper side) in a planar view.

As shown in FIGS. 3 and 4, the first filter 40 and the mirror part 50 are arranged in a direction (vertical direction) where radiation emitted from the radiation source 29 passes so that the first filter 40 is disposed on a side close to the radiation source 29 and the mirror part 50 is disposed on a side close to the imaging stand 16, between the radiation source 29 and the imaging stand 16.

Further, as shown in FIGS. 3 to 5, the moving part 30 of this embodiment includes a toothed gear 48 and a toothed gear 49 for moving the first filter 40 in the apparatus lateral direction, and a toothed gear 58 and a toothed gear 59 for moving the mirror part 50 in the apparatus lateral direction.

As shown in FIGS. 3 and 5, the first filter 40 includes an Rh (rhodium) filter 42 and an Al (aluminum) filter 44 that are arranged in the apparatus lateral direction. In the first filter 10 of this embodiment, for example, as shown in FIGS. 3 and 5, the Rh filter 42 and the Al filter 44 are fixed to a frame 41 using a screw or the like (not shown), and thus, a state where the Rh filter 42 is disposed on a left side in the apparatus lateral direction and the Al filter 44 is disposed on a right side is obtained.

The Rh filter 42 is a filter used in a case where normal imaging is performed. Generally, in imaging in the mammography apparatus 10, it is possible to clarify contrast of a radiation image captured using radiation of an energy component of 15 keV to 20 keV. In radiation of an energy component lower than the range (in a case where the energy component is smaller than 15 kev), since radiation exposure to a test subject (mammae) occurs, the radiation does not almost contribute to a radiation image. On the other hand, in radiation of an energy component higher than the range (in a case where the energy component exceeds 20 keV), since a transmittance at which the radiation passes through the test subject (mammae) is high, contrast of a captured radiation image may be lowered, which leads to deterioration in image quality. Since the Rh filter 42 shows 23.2 keV at a k absorption end, it is possible to reduce radiation of an energy component of 23.2 keV or greater, and to reduce radiation of a low energy component as the thickness becomes large, depending on the thickness. Accordingly, in the normal imaging of the mammography apparatus 10, by using the Rh filter 42, a spectrum of radiation to be emitted to a subject is set in an energy region of a desired range (15 keV to 20 keV). In this way, by using the Rh filter 42 in the normal imaging of the mammography apparatus 10, it is possible to reduce deterioration in image quality of a radiation image, and to reduce the amount of radiation exposure to a test subject.

On the other hand, since the Al filter 44 has a low attenuation factor of radiation compared with the Rh filter 42, the Al filter 44 is suitable for tomosynthesis imaging where imaging is performed in a short imaging time at each imaging position (irradiation time of radiation) while continuously moving the radiation source 29.

As shown in FIGS. 3 and 5, the shaft 46 where an axis line thereof extends along the apparatus lateral direction and opposite end portions thereof are supported on a housing of the radiation irradiation part 28 penetrates the holding member 47 that holds the frame 41 where the Rh filter 42 and the Al filter 44 are arranged. A gear is provided on an apparatus rear side of the holding member 47, and is engaged with the toothed gear 48. The gear 48 is engaged with the toothed gear 49. In this embodiment, by rotating the gear 49, the gear 48 is rotated. In accordance with the rotation of the gear 48, the first filter 40 held by the holding member 47 is moved in the lateral direction along the shaft 46, so that the first filter 40 is moved between the inside and the outside of an irradiation field 100 of radiation.

Further, the mirror part 50 of this embodiment includes a Cu (copper) filter 54 and a mirror 52 that are arranged in the direction (vertical direction) where radiation passes, as shown in FIGS. 3 to 5. The mirror 52 reflects visible light emitted from the visible light source 39 that is provided outside the radiation irradiation field 100 toward the imaging surface 24 of the imaging stand 16, so that the radiation irradiation field 100 (irradiation region) on the imaging surface 24 is suggested due to the visible light. On the other hand, the mirror 52 (mirror part 50) transmits radiation emitted from the radiation source 29.

For example, as shown in FIGS. 3 to 5, the Cu filter 54 is detachably attached to a rear surface (surface on the side of the radiation source 29) of the mirror 52 using a screw or the like (not shown). The Cu filter 54 of this embodiment is an example of a second filter of the present disclosure.

The Cu filter 54 is a filter used in a case where contrast imaging is performed. As a contrast medium used in the contrast imaging, an iodine contrast medium of which a k absorption end is 32 keV is generally used. In this contrast imaging, two times of imaging, that is, imaging in which radiation of an energy component lower than the k absorption end of the iodine contrast medium is emitted and imaging in which radiation of an energy component higher than the k absorption end of the iodine contrast medium is emitted are performed, a concentration distribution of the contrast medium is calculated from a difference of image data on the obtained two radiation images, and the contrast medium is imaged. Thus, in the contrast imaging, it is preferable to perform imaging using radiation having an energy component of 32 keV. By using the Cu filter 54, it is possible to set a state where quality of radiation to be emitted to a test subject has a preferable energy component. Further, by using the Cu filter 54, it is possible to reduce radiation of 32 keV or smaller, and thus, it is possible to reduce the amount of radiation exposure to the test subject.

As shown in FIGS. 3 and 5, a shaft 56 in which an axis line thereof extends along the apparatus lateral direction line and opposite end portions thereof are supported on the housing of the radiation irradiation part 28 penetrates a holding member 57 that holds the mirror 52. A gear is provided on the apparatus rear side of the holding member 57, and is engaged with the toothed gear 58. The gear 58 is engaged with the toothed gear 59. In this embodiment, by rotating the gear 59, the gear 58 is rotated. In accordance with the rotation of the gear 58, the mirror part 50 held on the holding member 57 is moved in the apparatus lateral direction along the shaft 56, so that the mirror part 50 is moved between the inside and the outside of the radiation irradiation field, independently of the first filter 40.

Next, a configuration of the radiation image capturing system 1 that includes the mammography apparatus 10 according to this embodiment will be described. The radiation image capturing system 1 of this embodiment has a function of performing capturing of a radiation image through an operation of a user such as a doctor or a radiation technician, on the basis of a command (imaging menu) input from an external system (for example, radiology information system (RIS)) through the console 6. In this embodiment, the technician, the doctor, or the like who performs imaging using the radiation image capturing system 1 (mammography apparatus 10) is referred to as a "user".

Figure 6:
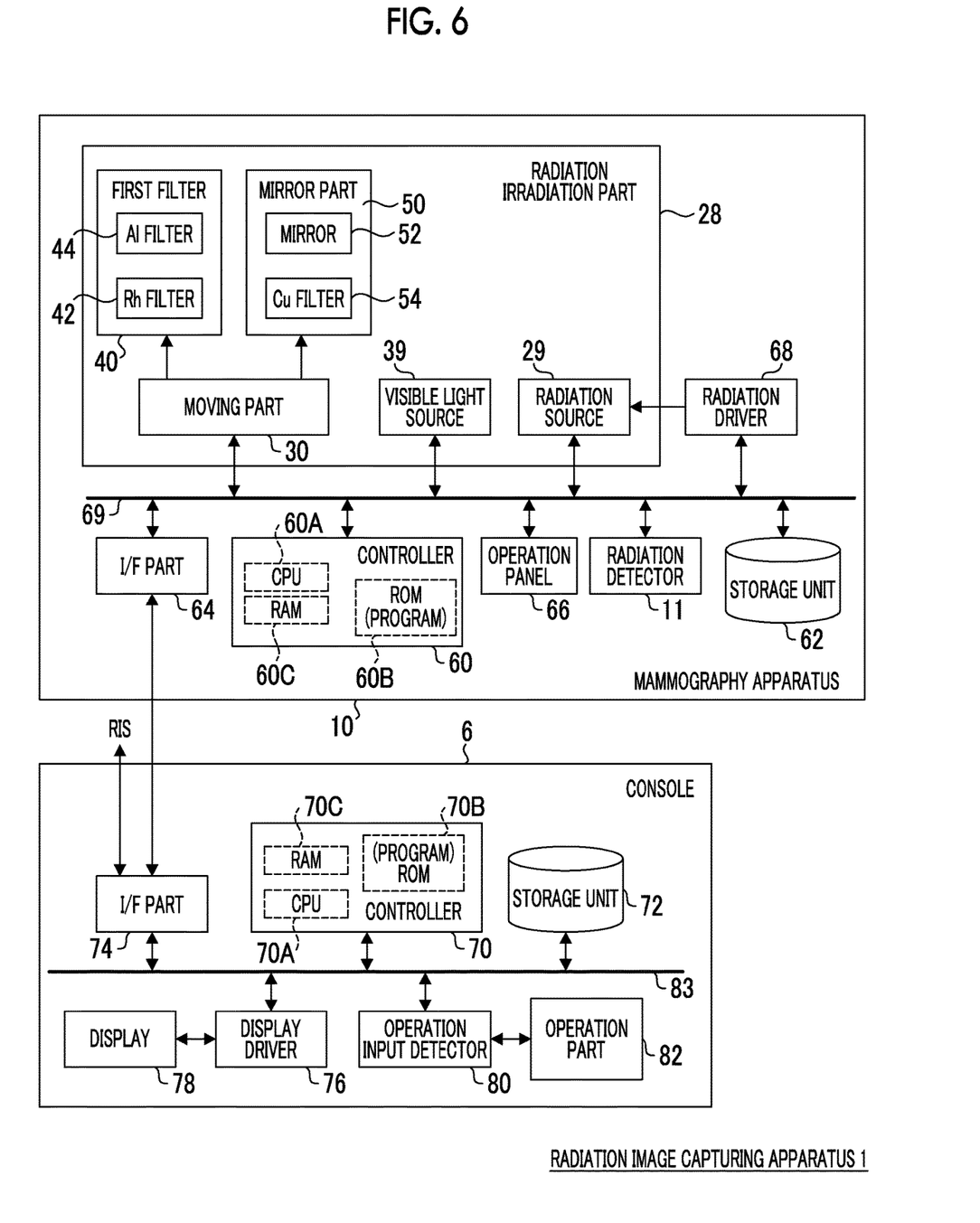
FIG. 6 is a block diagram showing an example of a configuration of a radiation image capturing system according to the first embodiment.

FIG. 6 is a block diagram showing an example of the configuration of the radiation image capturing system 1 of this embodiment. As shown in FIG. 6, the radiation image capturing system 1 of the embodiment includes the mammography apparatus 10 and the console 6.

The console 6 controls the mammography apparatus 10 using an imaging menu acquired from an external system or the like through a wireless communication local area network (LAN) or the like, a variety of other information, or the like.

The console 6 of the embodiment is a server computer, for example. As shown in FIG. 6, the console 6 includes a controller 70, a storage unit 72, an interface (I/F) part 74, a display driver 76, a display 78, an operation input detector 80, and an operation part 82. The controller 70, the storage unit 72, the interface (I/F) part 74, the display driver 76, and the operation input detector 80 are connected to each other to be able to exchange various types of information through a bus 83 such as a system bus or a control bus.

The controller 70 of this embodiment controls entire operations of the console 6. The controller 70 of this embodiment includes a central processing unit (CPU) 70A, a read only memory (ROM) 70B, and a random access memory (RAM) 70C. The ROM 70B stores various processing programs or the like executed by the CPU 70A in advance. The RAM 70C temporarily stores a variety of data.

The storage unit 72 stores image data on a radiation image captured by the mammography apparatus 10, a variety of other information, or the like. As a specific example of the storage unit 72, a hard disk drive (HDD), a solid state drive (SSD) or the like may be used.

The I/F part 74 performs communication of a variety of information between the mammography apparatus 10 or an external system such as an RIS through wireless communication or wired communication.

The display 78 displays a variety of information. The display drive 76 controls display of a variety of information on the display 78.

The operation part 82 is used when a user inputs a command relating to imaging or the like of a radiation image including a radiation exposure command, a variety of information, or the like.

The operation part 82 is not particularly limited, and for example, a variety of switches, a touch panel, a touch pen, a mouse, or the like may be used. The operation part 82 and the display 78 may be integrally used as a touch panel display. The operation input detector 80 detects an operation state with respect to the operation part 82.

On the other hand, as shown in FIG. 6, the mammography apparatus 10 of this embodiment includes a radiation detector 11, a radiation irradiation part 28, a controller 60, a storage unit 62, an I/F part 64, an operation panel 66, and a radiation source driver 68.

The radiation detector 11, the radiation irradiation part 28, the controller 60, the storage unit 62, the I/F part 64, the operation panel 66, and the radiation source driver 68 are connected to each other to be able to exchange a variety of information through a bus 69 such as a system bus or a control bus.

The controller 60 of this embodiment controls entire operations of the mammography apparatus 10. Further, the controller 60 of this embodiment controls the radiation detector 11 and the radiation irradiation part 28 in a case where capturing of a radiation image is performed. The controller 60 of this embodiment includes a CPU 60A, a ROM 60B, and a RAM 60C. The ROM 60B stores various programs or the like that are executed by the CPU 60A and include an imaging processing program (to be described later) in advance. The RAM 60C temporarily stores a variety of data.

In this embodiment, the various programs stored in the controller 60 of the mammography apparatus 10 and the controller 70 of the console 6 are stored in the ROMs (60B, 70B) of the controller 60 and the controller 70 in advance, but are not limited thereto. The various programs may be stored on a recording medium such as a compact disk read only memory (CD-ROM) or a removable disc, and may be installed into the ROM (60B, 70B) or the like from the recording medium. Further, the programs may be installed into the ROM (60B, 70B) from an external apparatus through a communication line such as the Internet.

As shown in FIG. 6, further, as described above, the radiation irradiation part 28 includes the radiation source 29, the moving part 30, the visible light source 39, the first filter 40, and the mirror part 50. The radiation source 29, the moving part 30, and the visible light source 39 are connected to the controller 60 through the bus 69. Thus, emission (irradiation) and non-emission (non-irradiation) of radiation from the radiation source 29 are controlled by the controller 60, and lighting and extinction of the visible light source 39 are controlled by the controller 60. In addition, as the controller 60 controls the moving part 30, as described above, the first filter 40 and the mirror part 50 are independently moved in the apparatus lateral direction.

The storage unit 62 stores image data on a radiation image captured by the radiation detector 11, a variety of different information, or the like. As a specific example of the storage unit 62, an HDD, an SSD, or the like may be used.

The I/F part 64 performs communication of a variety of information with the console 6 through wireless communication or wired communication.

The radiation source driver 68 rotates a shaft (not shown) provided in the above-described imaging part 12 to continuously move the radiation source 29 of the radiation irradiation part 28, to thereby change an incidence angle of radiation.

The operation panel 66 is provided on the imaging stand 16 of the mammography apparatus 10, for example, as a plurality of switches. The operation panel 66 may be provided as a touch panel.

Next, an operation of the mammography apparatus 10 of this embodiment will be described with reference to the drawings.

In the radiation image capturing system 1, in a case where imaging of mammae of a test subject is performed, first, a user positions the mammae of the test subject on the imaging surface 24 of the imaging stand 16 in the mammography apparatus 10, and presses and fixes the mammae between the imaging stand 16 and the pressing plate 20 using the pressing plate 20.

Figure 7:
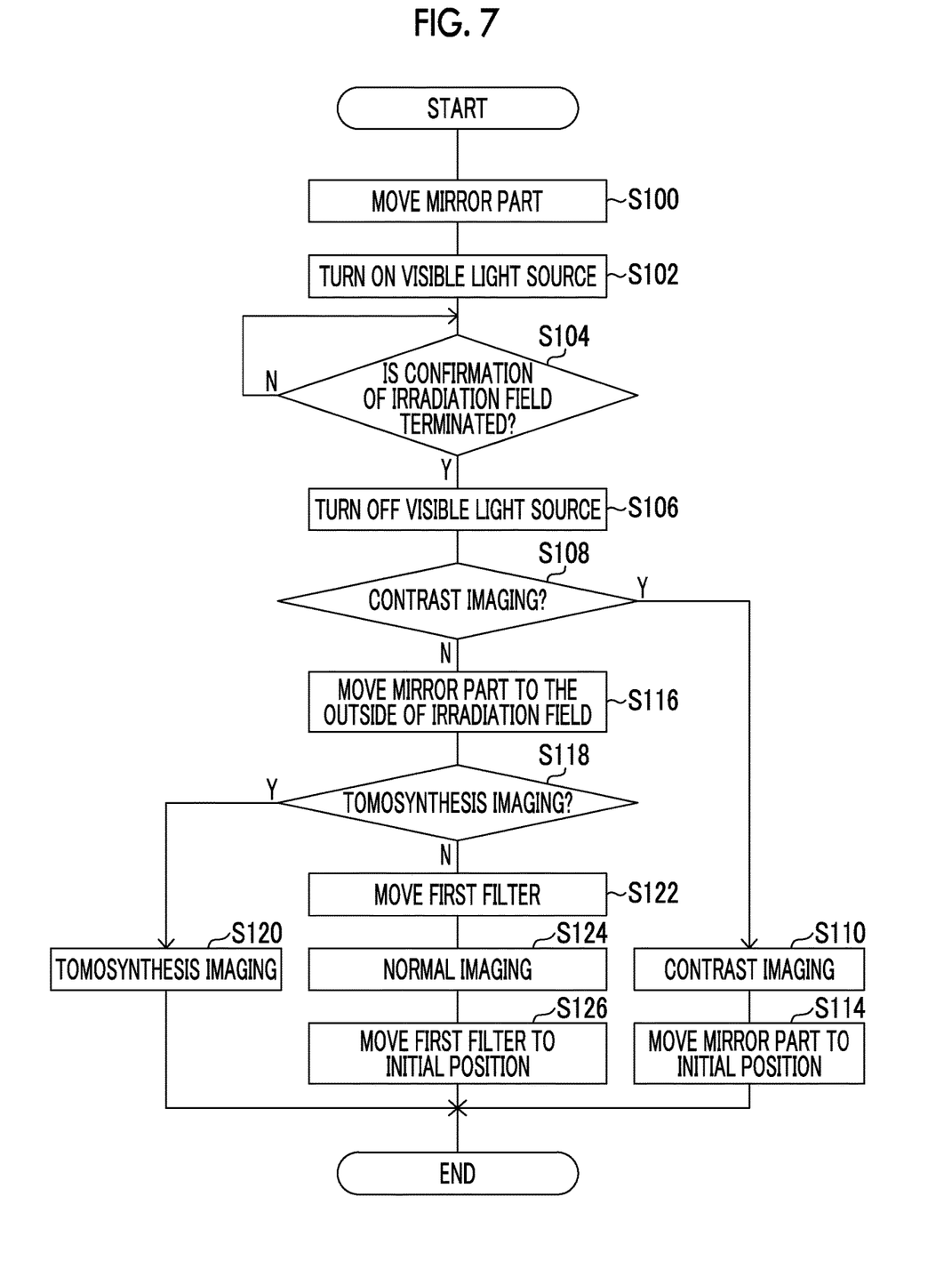
FIG. 7 is a flowchart showing an example of an imaging process executed by the mammography apparatus according to the first embodiment.

In a case where the user inputs a starting command of capturing of a radiation image through the operation part 82 of the console 6, the imaging starting command of imaging and an imaging menu are transmitted to the mammography apparatus 10 through the I/F part 74. In the mammography apparatus 10, in a case where the starting command of imaging of a radiation image and the imaging menu are received from the console 6, an imaging process is executed. FIG. 7 is a flowchart showing an example of a flow of an imaging process executed by the controller 60 of the mammography apparatus 10 of this embodiment. In the mammography apparatus 10 of this embodiment, the CPU 60A of the controller 60 executes an imaging processing program stored in the ROM 60B to executes the imaging process shown in FIG. 7.

In step S100, the controller 60 moves the mirror part 50 from an initial position that is a position outside the irradiation field 100 to a predetermined position inside the irradiation field 100 using the moving part 30. In the mammography apparatus 10 of this embodiment, a user first confirms the irradiation field 100 using visible light emitted from the visible light source 39 before radiation is emitted from the radiation source 29. Thus, in step S100, the controller 60 sets the mirror 52 of the mirror part 50 to a predetermined position for suggesting the irradiation field 100.

Figure 8:
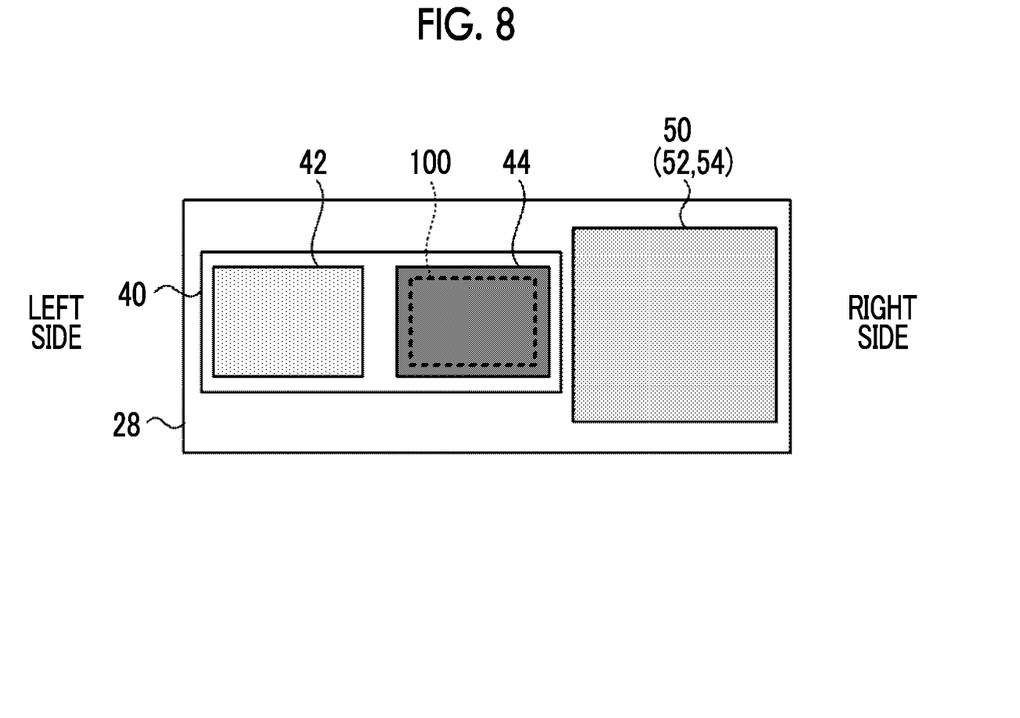
FIG. 8 is a schematic diagram showing an example of an initial position of the first filter and the mirror part and an arrangement thereof in tomosynthesis imaging.

In this embodiment, when the imaging process shown in FIG. 7 is initially executed, the first filter 40 and the mirror part 50 are positioned at an initial position. FIG. 8 schematically shows an example of the initial position of the first filter 40 and the mirror part 50. As shown in FIG. 8, in the mammography apparatus 10 of this embodiment, a state where the first filter 40 and the mirror part 50 are arranged in the apparatus lateral direction without overlapping so that the first filter 40 is disposed on a left side in the apparatus lateral direction and the mirror part 50 is disposed on a right side in the apparatus lateral direction.

Figure 9:
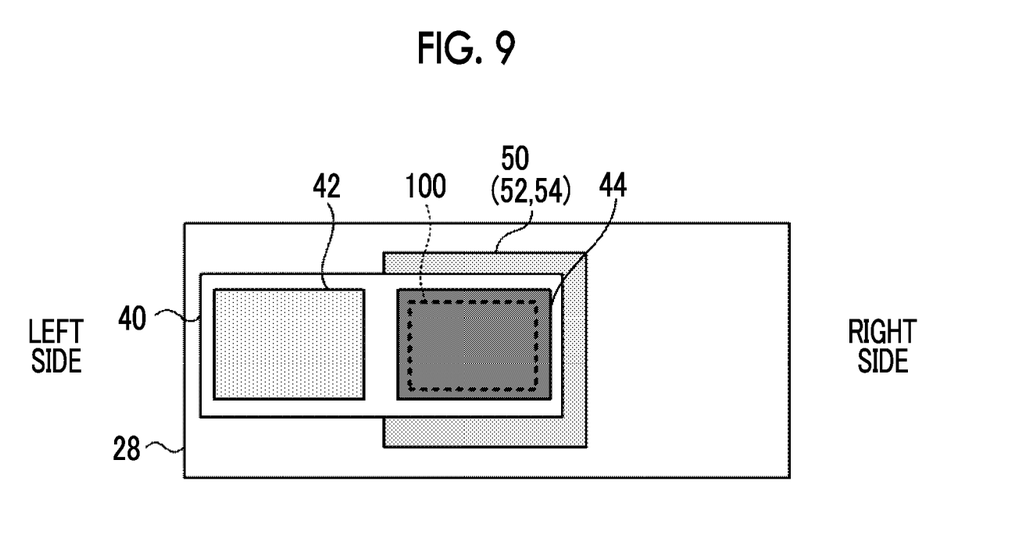
FIG. 9 is a schematic diagram showing an example of an arrangement of the first filter and the mirror part in check of an irradiation field.

On the other hand, in a case where the confirmation of the irradiation field 100 is performed, as schematically shown in FIG. 9, the mirror part 50 (mirror 52) is disposed at a position inside the irradiation field 100. Specifically, the mirror part 50 is disposed at a position where an irradiation field of visible light on the imaging surface 24 and the irradiation field 100 of radiation emitted to the imaging surface 24 become equal to each other as the visible light emitted from the visible light source 39 is reflected from the mirror 52.

In the next step S102, the controller 60 turns on the visible light source 39. Thus, on the imaging surface 24, the radiation irradiation field 100 of the radiation is suggested by the visible light reflected from the mirror 52 of the mirror part 50.

In the next step S104, the controller 60 determines whether the confirmation of the irradiation field 100 is terminated by the user. In the mammography apparatus 10 of this embodiment, in a case where the confirmation of the irradiation field 100 is terminated, the user inputs a command indicating that the confirmation of the irradiation field 100 is terminated through the operation panel 66 of the mammography apparatus 10. Thus, the controller 60 determines whether the confirmation of the irradiation field 100 is terminated according to whether the command indicating that the confirmation of the irradiation field 100 is terminated is input through the operation panel 66.

In a case where the confirmation of the irradiation field 100 is not terminated, the determination in step S104 is negative, and then, this step is repeated. On the other hand, in a case where the confirmation of the irradiation field 100 is terminated, the determination in step S104 is affirmative, and then, the procedure proceeds to step S106.

In step S106, the controller 60 turns off the visible light source 39.

In the next step S108, the controller 60 determines whether contrast imaging is performed. A method for determining whether the contrast imaging is performed in the controller 60 is not particularly limited. For example, in a case where information indicating the kind of imaging is included in an imaging menu received from the console 6, it may be determined whether the contrast imaging is performed on the basis of the information indicating the kind of imaging. Further, for example, in a case where the contrast imaging is performed as described above, an energy component of radiation emitted to a test subject from the radiation source 29 is set to be higher than that in a case where simple imaging is performed. Thus, a tube voltage applied to the radiation source 29 is higher than that in a case where the simple imaging is performed. Accordingly, the controller 60 may determine whether the contrast imaging is performed according to whether a tube voltage included in the imaging menu is a tube voltage for the contrast imaging. Further, for example, in a case where the user inputs a command indicating that the contrast imaging is performed through the operation panel 66 of the mammography apparatus 10 or the operation part 82 of the console 6, the controller 60 may determine whether the contrast imaging is performed according to the command of the user.

In a case where the contrast imaging is performed, the determination in step S108 is affirmative, and then, the procedure proceeds to step S110. In step S110, the controller 60 executes the contrast imaging. A method for the contrast imaging performed in this step is not particularly limited, and may be a general contrast imaging method.

Figure 10:
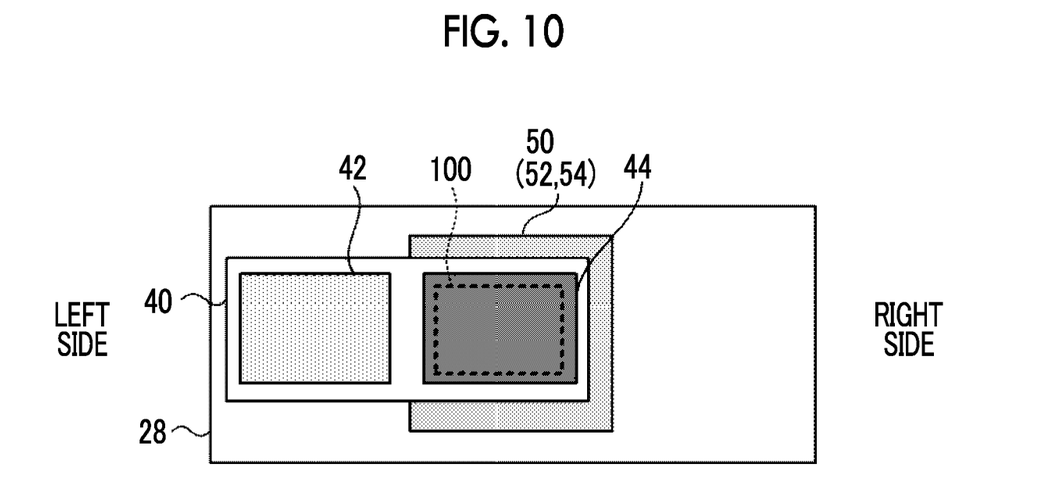
FIG. 10 is a schematic diagram showing an example of an arrangement of the first filter and the mirror part in contrast imaging.

In the mammography apparatus 10 of this embodiment, as described above, in a case where the contrast imaging is performed, the imaging is performed using the Cu filter 54. Thus, as schematically shown in FIG. 10, the Cu filter 54 is disposed at a position inside the irradiation field 100. Specifically, the Cu filter 54 is disposed at a position in a state where the irradiation field 100 is covered with the entirety of the Cu filter 54. In the mammography apparatus 10 of this embodiment, as shown in FIG. 10, in a case where the contrast imaging is performed, the Al filter 44 is used in addition to the Cu filter 54, but the contrast imaging may be performed without using the Al filter 44 differently from this embodiment.

As shown in FIG. 10, positions of the first filter 40 and the mirror part 50 in a case where the contrast imaging is performed and positions (see FIG. 9) of the first filter 40 and the mirror part 50 in a case where the confirmation of the irradiation field 100 is performed are the same. Thus, as in this embodiment, in a case where the contrast imaging is subsequently performed after the confirmation of the irradiation field 100 is performed, the movement of the first filter 40 and the mirror part 50 is not performed.

In a case where the contrast imaging in step S110 is terminated, a captured radiation image is output to the console 6 from the mammography apparatus 10.

In the next step S114, the controller 60 moves the mirror part 50 to the initial position (see FIG. 8) using the moving part 30, and then, terminates the imaging process.

On the other hand, in a case where the determination in step S108 is negative (in a case where it is determined that the contrast imaging is not performed), the procedure proceeds to step S116.

In step S116, the controller 60 moves the mirror part 50 to the outside of the irradiation field 100 using the moving part 30. In this embodiment, for example, the controller 60 moves the mirror part 50 to the initial position (see FIG. 8).

In the next step S118, the controller 60 determines whether tomosynthesis imaging is performed. A method for determining whether the tomosynthesis imaging is performed in the controller 60 is not particularly limited. For example, in a case where information indicating the kind of imaging is included in an imaging menu received from the console 6, it may be determined whether the tomosynthesis imaging is performed on the basis of the information indicating the kind of imaging. Further, for example, in a case where the tomosynthesis imaging is performed as described above, since the imaging is performed plural times while moving the radiation source 29, it may be determined whether the tomosynthesis imaging is performed on the basis of information indicating a command for movement of the radiation source 29, a command for change of the times of imaging, or the like included in the imaging menu.

In a case where the tomosynthesis imaging is performed, the determination in step S118 is affirmative, and then, the procedure proceeds to step S120. In step S120, the controller 60 executes the tomosynthesis imaging. A method for the tomosynthesis imaging performed in this step is not particularly limited, and may be a general tomosynthesis imaging method.

In the mammography apparatus 10 of this embodiment, as described above, in a case where the tomosynthesis imaging is performed, the imaging is performed using the Al filter 44. Thus, the Al filter 44 is disposed at a position inside the irradiation field 100. Specifically, the Al filter 44 is disposed in a state where the irradiation field 100 is covered with the entirety of the Al filter 44. That is, in the mammography apparatus 10 of this embodiment, in a case where the tomosynthesis imaging is performed, as schematically shown in FIG. 8, the first filter 40 and the mirror part 50 are arranged in a similar way to the initial position. At a timing when step S120 is executed, the first filter 40 and the mirror part 50 are positioned at the initial position.

In a case where the tomosynthesis imaging in step S120 is terminated, a captured radiation image is output to the console 6 from the mammography apparatus 10. As described above, in the case of the tomosynthesis imaging, since the first filter 40 and the mirror part 50 are arranged at the initial position, in a case where the step S120 is terminated, the controller 60 terminates the imaging process.

On the other hand, in a case where the tomosynthesis imaging or the normal imaging is performed, the determination in step S118 is negative, and then, the procedure proceeds to step S122.

Figure 11:
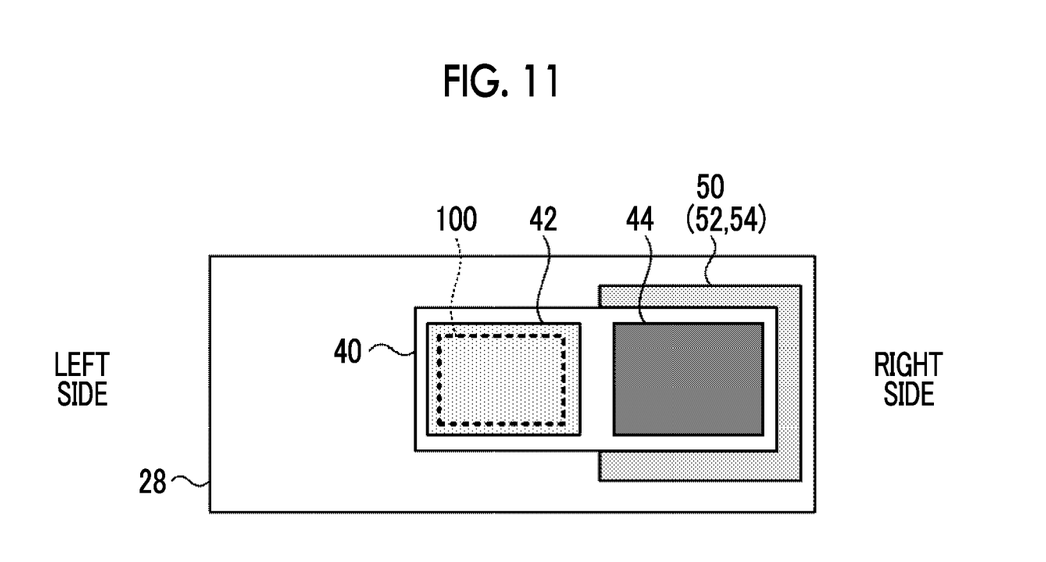
FIG. 11 is a schematic diagram showing an example of an arrangement of the first filter and the mirror part in normal imaging.

In step S122, the controller 60 moves the first filter 40 to a position inside the irradiation field 100 using the moving part 30. In the mammography apparatus 10 of this embodiment, as described above, in a case where the normal imaging is performed, the imaging is performed using the Rh filter 42. Thus, as schematically shown in FIG. 11, the Rh filter 42 is disposed at a position inside the irradiation field 100. Specifically, the controller 60 moves the first filter 40 so that the Rh filter 42 is disposed at a position in a state where the irradiation field 100 is covered with the entirety of the Rh filter 42.

In the next step S124, the controller 60 executes the normal imaging. A method of the normal imaging performed in this step is not particularly limited, and may be a general normal imaging method according to imaging menus. In a case where the normal imaging is terminated, a captured radiation image is output to the console 6 from the mammography apparatus 10.

In the next step S126, the controller 60 moves the first filter 40 to the initial position (see FIG. 8) using the moving part 30, and then, terminates the imaging process.

In this way, the mammography apparatus 10 of this embodiment includes the radiation source 29 that emits radiation toward the imaging stand 16, the visible light source 39 that is provided outside the irradiation field 100 of the radiation emitted from the radiation source 29 and emits visible light, the first filter 40 that includes the Rh filter 42 and the Al filter 44 as a plurality of filters that is selectively used according to the kind of imaging, and the mirror part 50 that is provided between the radiation source 29 and the imaging stand 16, includes the Cu filter 54 used in a case where contrast imaging is performed, reflects the visible light toward the imaging stand 16, and is movable between a position inside the irradiation field 100 and a position outside the irradiation field 100.

Second Embodiment

As described above, a tube voltage varies according to the kind of imaging, and the Cu filter 54 of the mirror part 50 is used in a case where the tube voltage applied to the radiation source 29 is high, compared with the Rh filter 42 and the Al filter 44. For example, as described above, the tube voltage applied to the radiation source 29 in a case where contrast imaging is performed is higher than a tube voltage applied to the radiation source 29 in a case where simple imaging is performed. Thus, in the mammography apparatus 10 of this embodiment, filters (Rh filter 42, Al filter 44, and Cu filter 54) used for imaging are arranged according to tube voltages applied to the radiation source 29.

Since a configuration of the mammography apparatus 10 is the same as in the first embodiment, description thereof will not be repeated. In this embodiment, since a partial process of an imaging process executed by the controller 60 of the mammography apparatus 10 is different from the imaging process (see FIG. 7) in the first embodiment, the different process will be described.

Figure 12:
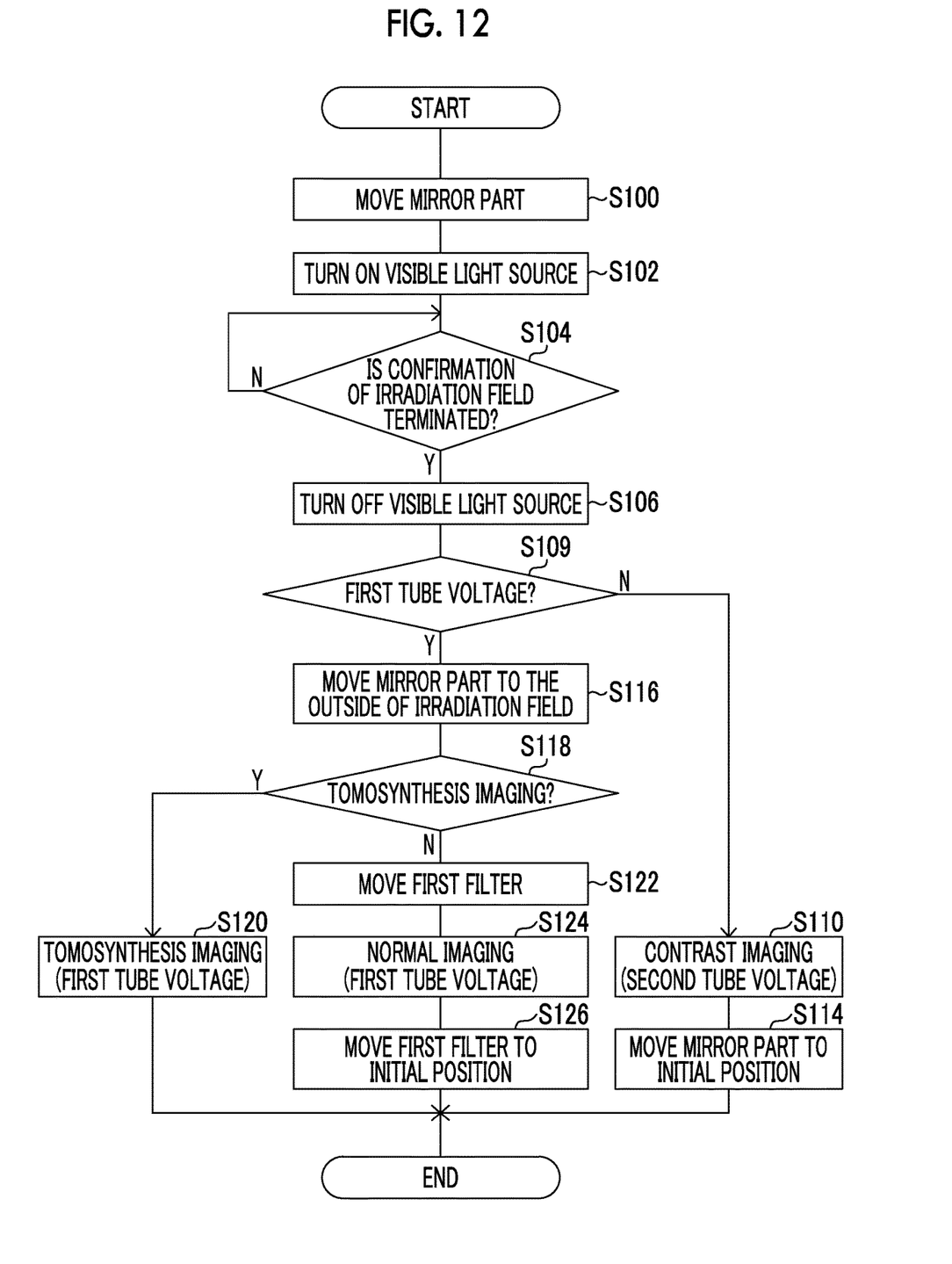
FIG. 12 is a flowchart showing an example of an imaging process executed by a mammography apparatus according to a second embodiment.

FIG. 12 is a flowchart showing an example of a flow of the imaging process executed by the controller 60 of the mammography apparatus 10 of this embodiment. The imaging process shown in FIG. 12 is different from the imaging process (see FIG. 7) in the first embodiment in that a process of step S109 is performed instead of the process of step S108 in the imaging process (see FIG. 7) in the first embodiment.

In step S109, the controller 60 determines whether a tube voltage applied to the radiation source 29 is a first tube voltage in capturing of a radiation image. A method for determining whether the first tube voltage is applied in the controller 60 is not particularly limited. For example, a tube voltage in imaging to which the first filter 40 is applied may be determined as the first tube voltage in advance, and in a case where information indicating a tube voltage is included in an imaging menu received from the console 6, the controller 60 may determine whether the first tube voltage is applied on the basis of the information indicating the tube voltage. The first tube voltage may not correspond to only a specific tube voltage (for example, 20 kVp). For example, the first tube voltage may include a tube voltage in imaging to which the Rh filter 42 is applied, and a tube voltage in imaging to which the Al filter 44 is applied.

Further, for example, as described above, in a case where simple imaging is performed, a tube voltage applied to the radiation source 29 is lower than that in a case where contrast imaging is performed. Thus, the controller 60 may determine whether the tube voltage is the first tube voltage by considering a tube voltage lower than the tube voltage for the contrast imaging or the tube voltage for the contrast imaging as the first tube voltage.

In a case where the tube voltage applied to the radiation source 29 is not the first tube voltage, that is, in a case where the tube voltage applied to the radiation source 29 is a second tube voltage, the determination in step S109 is negative, and then, the procedure proceeds to step S110. Then, the controller 60 applies the second tube voltage to the radiation source 29 to execute the contrast imaging.

On the other hand, in a case where the tube voltage applied to the radiation source 29 is the first tube voltage, the determination in step S109 is affirmative, and then, the procedure proceeds to step S116. In this case, after step S120, the controller 60 applies the first tube voltage to the radiation source 29 to execute tomosynthesis imaging. Further, after step S124, the controller 60 applies the first tube voltage to the radiation source 29 to execute normal imaging.

In this way, the mammography apparatus 10 of this embodiment includes the radiation source 29 that emits radiation generated by application of a tube voltage toward the imaging stand 16, the visible light source 39 that is provided outside the irradiation field 100 of the radiation emitted from the radiation source 29 and emits visible light, the first filter 40 that is provided between the radiation source 29 and the imaging stand 16 and includes the Rh filter 42 and the Al filter 44 as a plurality of filters that is selectively used in a case where the first tube voltage is applied to the radiation source 29, and a mirror part 50 that is provided between the radiation source 29 and the imaging stand 16, includes the Cu filter 54 used in a case where the second tube voltage different from the first tube voltage is applied to the radiation source 29, reflects the visible light toward the imaging stand 16, and is movable between a position inside the irradiation field 100 and a position outside the irradiation field 100.

As described above, according to the mammography apparatus 10 of each of the above-described embodiments, since the mirror part 50 includes the mirror 52 and the Cu filter 54, it is possible to reduce an increase in the size of the entirety of the mammography apparatus 10, compared with a case where the mirror 52 and the Cu filter 54 are individually provided.

In a case where the Cu filter 54 is provided in the mirror 52 that reflects visible light in a mammography apparatus that does not include a filter (Cu filter 54) for performing contrast imaging to suggest the irradiation field 100, it is possible to cope with the contrast imaging, and thus, it is possible to easily add a function of contrast imaging to the existing mammography apparatus that does not have a function of contrast imaging, and to reduce the cost thereof.

In each of the above-described embodiments, a case where the Cu filter 54 is provided in the mirror 52 has been described, but the invention is not limited thereto. For example, in a case where the mammography apparatus 10 includes the Cu filter 54 but does not include the mirror 52, for example, in a case where the mammography apparatus 10 already has the contrast imaging function, a configuration in which the mirror 52 is fixedly attached to the existing Cu filter 54 using a screw or the like, a configuration in which an Al film is, for example, vapor-deposited on a rear surface of the Cu filter 54 (a surface thereof on the side of the imaging surface 24) to assign a function as the mirror 52, may be used, for example.

Further, in the mammography apparatus 10 of each of the above-described embodiments, a configuration in which the Rh filter 42 and the Al filter 44 are provided as filters included in the first filter 40 and the Cu filter 54 is provided as a filter included in the mirror part 50 has been described, but filters included in the mammography apparatus 10 are not particularly limited. The filters included in the mammography apparatus 10 may be different from each other in at least one of an absorbance of radiation to be transmitted, an attenuation factor of the radiation, or an energy component of absorption to be absorbed. For example, the filters may employ an Ag (silver) filter, a Mo (molybdenum) filter, or the like, and may employ various filters based on a bulb of the radiation source 29 or the like.

In each of the above-described embodiments, a configuration (see FIG. 8) in which a state where the first filter 40 and the mirror part 50 are arranged in the apparatus lateral direction without overlapping so that the first filter 40 is disposed on the left side in the apparatus lateral direction of the mammography apparatus 10 and the mirror part 50 is disposed on the right side in the apparatus lateral direction is an initial position has been described, but the initial position of the first filter 40 and the mirror part 50 is not particularly limited. For example, as described above, a state where the first filter 40 is disposed on the left side in the apparatus lateral direction of the mammography apparatus 10 and the mirror part 50 (mirror 52) is disposed at a position inside the irradiation field 100 (see FIG. 9 or 10) may be set as the initial position. In this case, step S100 of the above-described imaging process (FIGS. 7 and 12) may be removed. Further, in this case, in the contrast imaging (step S110), the first filter 40 and the mirror part 50 may not be moved in the imaging process. On the other hand, in this case, in the tomosynthesis imaging (step S120) and the normal imaging (step S124), the mirror part 50 is moved to the initial position after each imaging process, and then, the imaging process is terminated.

The radiation in each of the above-described embodiment is not particularly limited, and X-rays, γ-rays, or the like may be used.

The configurations, operations, and the like of the radiation image capturing system 1, the console 6, the mammography apparatus 10, and the like described in each of the above-described embodiments are examples, and may be modified in accordance with situations in a range without departing from the concept of the invention.

EXPLANATION OF REFERENCES

1: radiation image capturing system
6: console
10: mammography apparatus
11: radiation detector
11A: detection surface
12: imaging part
14: base stand part
16: imaging stand
18: operation part
20: pressing plate
22: support part
24: imaging surface
26: support arm
28: radiation irradiation part
29: radiation source
30: moving part
39: visible light source
40: first filter
41: frame
42: Rh filter
44: Al filter
46: shift
47: holding member
48, 49, 58, 59: gear
50: mirror part
52: mirror
54: Cu filter
56: shaft
57: holding member
60, 70: controller
60A, 70A: CPU
60B, 70B: ROM
60C, 70C: RAM
62, 72: storage unit
64, 74: I/F part
66: operation panel
68: radiation source driver
69, 83: bus
76: display driver
78: display
80: operation input detector
82: operation part
100: irradiation field CL: normal line
RC: radiation axis
α: angle

What is claimed is:

1. A mammography apparatus comprising:
a radiation source that emits radiation generated by application of a tube voltage toward an imaging stand;
a visible light source that is provided outside an irradiation field of the radiation emitted from the radiation source and emits visible light;
a first filter that is provided between the radiation source and the imaging stand and includes a plurality of filters selectively used in a case where a first tube voltage is applied to the radiation source;
a mirror part, composed of a second filter and a mirror, that is provided between the radiation source and the imaging stand, the second filter being disposed at the radiation source side of the mirror and being used in a case where a second tube voltage different from the first tube voltage is applied to the radiation source, the mirror being disposed opposite to the radiation source side, reflecting the visible light toward the imaging stand, and being configured to transmit the radiation emitted by the radiation source,
a first moving part that moves the first filter so as to switch between a position inside the irradiation field and a position outside the irradiation field; and
a second moving part that moves the mirror part independently from the first moving part, so as to switch between the position inside the irradiation field and the position outside the irradiation field.

2. The mammography apparatus according to claim 1, wherein the second tube voltage is a tube voltage used in contrast imaging.

3. The mammography apparatus according to claim 1, wherein the second tube voltage is a tube voltage higher than the first tube voltage.

4. The mammography apparatus according to claim 1, wherein the first filter and the second filter are different from each other in at least one of an absorbance of radiation to be transmitted, an attenuation factor of the radiation, or an energy component of radiation to be absorbed.

5. The mammography apparatus according to claim 1, wherein the mirror part is configured so that the second filter is disposed on the side of the radiation source and the visible light is emitted toward the imaging stand from the visible light source.

6. The mammography apparatus according to claim 1, wherein the plurality of filters includes a filter used for tomosynthesis imaging.

7. The mammography apparatus according to claim 1, wherein the second filter is a filter made of copper.

8. The mammography apparatus according to claim 1, wherein the second moving part sets the position of the mirror part to the position inside the irradiation field in a state where the radiation source does not emit radiation, and sets the position of the mirror part to the position outside the irradiation field in a state where the radiation source emits radiation and the first filter is used.

9. The mammography apparatus according to claim 1, wherein the second moving part sets the position of the mirror part to the position inside the irradiation field in a state where the radiation source does not emit radiation, and sets the position of the mirror part to the position inside the irradiation field in a state where the radiation source emits radiation and the second filter is used.

10. The mammography apparatus according to claim 1, wherein the first moving part moves in an apparatus lateral direction to switch the first filter between a position inside the irradiation field and a position outside the irradiation field.

11. The mammography apparatus according to claim 1, wherein the second moving part moves in an apparatus lateral direction to switch the mirror part between a position inside the irradiation field and a position outside the irradiation field.

12. A mammography apparatus comprising:
a radiation source that emits radiation toward an imaging stand;
a visible light source that is provided outside an irradiation field of the radiation emitted from the radiation source and emits visible light;
a first filter that includes a plurality of filters selectively used according to a type of imaging;
a mirror part, composed of a second filter and a mirror, that is provided between the radiation source and the imaging stand, the second filter being disposed at the radiation source side of the mirror and being used in a case where contrast imaging is performed, the mirror being disposed opposite to the radiation source side and configured to reflect the visible light toward the imaging stand, the mirror part being movable between a position inside the irradiation field and a position outside the irradiation field, and being configured to transmit the radiation emitted by the radiation source,
a first moving part that moves the first filter so as to switch between a position inside the irradiation field and a position outside the irradiation field; and
a second moving part that moves the mirror part independently from the first moving part, so as to switch between the position inside the irradiation field and the position outside the irradiation field.

13. The mammography apparatus according to claim 12, wherein the first moving part moves in an apparatus lateral direction to switch the first filter between a position inside the irradiation field and a position outside the irradiation field.

14. The mammography apparatus according to claim 12, wherein the second moving part moves in an apparatus lateral direction to switch the mirror part between a position inside the irradiation field and a position outside the irradiation field.

* * * * *